US011812967B2

(12) United States Patent
Andrews et al.

(10) Patent No.: US 11,812,967 B2
(45) Date of Patent: Nov. 14, 2023

(54) ANEURYSM TREATMENT COILS AND ASSOCIATED SYSTEMS AND METHODS OF USE

(71) Applicant: Covidien LP, Mansfield, MA (US)

(72) Inventors: Christopher Andrews, Lake Elsinore, CA (US); Etelvina Rivas, Anaheim, CA (US); Hieu Dang, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 457 days.

(21) Appl. No.: 17/247,551

(22) Filed: Dec. 16, 2020

(65) Prior Publication Data
US 2021/0100557 A1 Apr. 8, 2021

Related U.S. Application Data

(62) Division of application No. 16/108,434, filed on Aug. 22, 2018, now Pat. No. 10,905,432.

(51) Int. Cl.
*A61B 17/12* (2006.01)

(52) U.S. Cl.
CPC .... *A61B 17/12113* (2013.01); *A61B 17/1214* (2013.01); *A61B 17/12031* (2013.01); *A61B 2017/12054* (2013.01)

(58) Field of Classification Search
CPC .......... A61B 17/12113; A61B 17/1214; A61B 17/12031; A61B 17/12054; A61B 2017/00526
See application file for complete search history.

(56) References Cited

U.S. PATENT DOCUMENTS 5,304,194 A * 4/1994 Chee ................ A61B 17/12022
606/198
5,354,295 A 10/1994 Guglielmi et al.
(Continued)

FOREIGN PATENT DOCUMENTS

CN 102302377 B 6/2014
EP 1698284 A1 9/2006
(Continued)

OTHER PUBLICATIONS

Codman Neurovascular, "Codman Neurovascular Microcoils" Brochure, Codman & Shurtleff, Inc., Raynham, MA, 2012.
(Continued)

*Primary Examiner* — Phong Son H Dang
(74) *Attorney, Agent, or Firm* — FORTEM IP LLP; Mary Fox (57) ABSTRACT

Devices, systems, and methods for treating vascular defects are disclosed herein. One aspect of the present technology, for example, is directed toward an occlusive device comprising a coil having a proximal end, a distal end, and a longitudinal axis extending therebetween. The coil may be formed of an elongated member wound about the longitudinal axis of the coil in a series of contiguous loops, wherein each of the loops extend around the longitudinal axis between a first end and a second end. The second end may be disposed at generally the same angular position as the first end about to the longitudinal axis of the coil. The elongated member may undulate along its longitudinal axis between the first and second ends of at least some of the individual loops.

20 Claims, 6 Drawing Sheets

(56) References Cited

U.S. PATENT DOCUMENTS

| | | | |
|---|---|---|---|
| 5,649,949 A * | 7/1997 | Wallace | A61B 17/1215 606/198 |
| 5,658,308 A * | 8/1997 | Snyder | A61B 17/12145 606/198 |
| 5,669,931 A * | 9/1997 | Kupiecki | A61B 17/12145 606/198 |
| 5,749,891 A * | 5/1998 | Ken | A61B 17/12113 606/191 |
| 5,797,953 A * | 8/1998 | Tekulve | A61B 17/12145 623/1.22 |
| 5,800,454 A * | 9/1998 | Jacobsen | A61B 17/12172 606/198 |
| D407,818 S * | 4/1999 | Mariant | D24/143 |
| 5,951,599 A | 9/1999 | McCrory | |
| 6,013,084 A * | 1/2000 | Ken | A61B 17/12113 606/191 |
| D421,304 S * | 2/2000 | Mariant | D24/143 |
| 6,024,765 A * | 2/2000 | Wallace | A61B 17/12022 606/191 |
| 6,143,007 A * | 11/2000 | Mariant | A61B 17/12022 606/151 |
| 6,280,457 B1 * | 8/2001 | Wallace | A61B 17/12145 606/191 |
| 6,309,367 B1 | 10/2001 | Boock | |
| 6,602,261 B2 | 8/2003 | Greene et al. | |
| 6,605,101 B1 | 8/2003 | Schaefer et al. | |
| 6,878,384 B2 | 4/2005 | Cruise et al. | |
| 7,033,374 B2 | 4/2006 | Schaefer et al. | |
| 7,229,461 B2 | 6/2007 | Chin et al. | |
| 7,601,160 B2 | 10/2009 | Richter | |
| 7,846,198 B2 | 12/2010 | Hogendijk | |
| 7,955,344 B2 * | 6/2011 | Finitsis | A61B 17/32056 606/159 |
| RE42,625 E | 8/2011 | Guglielmi | |
| 7,988,723 B2 | 8/2011 | Beach et al. | |
| 8,043,326 B2 | 10/2011 | Hancock et al. | |
| 8,377,091 B2 | 2/2013 | Cruise et al. | |
| 8,425,541 B2 | 4/2013 | Masters et al. | |
| 8,470,013 B2 | 6/2013 | Duggal et al. | |
| 8,535,345 B2 * | 9/2013 | Desai | A61B 17/12154 606/200 |
| 8,715,317 B1 | 5/2014 | Janardhan et al. | |
| 8,870,908 B2 | 10/2014 | Labdag et al. | |
| 8,906,057 B2 | 12/2014 | Connor et al. | |
| 9,211,202 B2 | 12/2015 | Strother et al. | |
| 9,456,823 B2 * | 10/2016 | Constant | A61B 90/39 |
| 9,486,224 B2 | 11/2016 | Riina et al. | |
| 9,636,118 B2 | 5/2017 | Garza et al. | |
| 9,833,309 B2 | 12/2017 | Levi et al. | |
| 9,844,380 B2 | 12/2017 | Furey | |
| 9,907,684 B2 | 3/2018 | Connor et al. | |
| 9,962,146 B2 | 5/2018 | Hebert et al. | |
| 9,993,252 B2 | 6/2018 | Keeley et al. | |
| 10,028,745 B2 | 7/2018 | Morsi | |
| 10,905,432 B2 | 2/2021 | Andrews et al. | |
| 10,912,569 B2 | 2/2021 | Andrews et al. | |
| 2001/0000797 A1 | 5/2001 | Mazzocchi | |
| 2001/0001835 A1 | 5/2001 | Greene et al. | |
| 2002/0107534 A1 * | 8/2002 | Schaefer | A61B 17/12113 606/151 |
| 2003/0018294 A1 | 1/2003 | Cox | |
| 2003/0028209 A1 | 2/2003 | Teoh et al. | |
| 2003/0040772 A1 | 2/2003 | Hyodoh et al. | |
| 2003/0195609 A1 | 10/2003 | Berenstein et al. | |
| 2005/0149109 A1 | 7/2005 | Wallace et al. | |
| 2005/0192618 A1 | 9/2005 | Porter | |
| 2005/0246008 A1 | 11/2005 | Hogendijk et al. | |
| 2005/0267511 A1 | 12/2005 | Marks et al. | |
| 2006/0155323 A1 | 7/2006 | Porter et al. | |
| 2006/0200234 A1 | 9/2006 | Hines | |
| 2006/0206199 A1 | 9/2006 | Churchwell et al. | |
| 2006/0241686 A1 * | 10/2006 | Ferrera | A61B 17/12022 606/200 |
| 2007/0100426 A1 | 5/2007 | Rudakov et al. | |
| 2007/0175536 A1 * | 8/2007 | Monetti | A61B 17/1214 140/102.5 |
| 2007/0191924 A1 | 8/2007 | Rudakov | |
| 2007/0225738 A1 | 9/2007 | Pal | |
| 2007/0299464 A1 * | 12/2007 | Cruise | A61B 17/12168 128/831 |
| 2008/0114391 A1 | 5/2008 | Dieck et al. | |
| 2010/0144895 A1 | 6/2010 | Porter | |
| 2011/0137405 A1 | 6/2011 | Wilson et al. | |
| 2012/0150147 A1 | 6/2012 | Leynov et al. | |
| 2012/0296408 A1 * | 11/2012 | Jones | A61B 17/12 623/1.11 |
| 2012/0310271 A1 | 12/2012 | Kwon | |
| 2012/0316632 A1 | 12/2012 | Gao | |
| 2013/0274866 A1 | 10/2013 | Cox et al. | |
| 2014/0012307 A1 | 1/2014 | Franano et al. | |
| 2014/0058420 A1 | 2/2014 | Hannes et al. | |
| 2014/0316012 A1 | 10/2014 | Freyman et al. | |
| 2014/0371734 A1 | 12/2014 | Truckai | |
| 2015/0216684 A1 | 8/2015 | Enzmann et al. | |
| 2015/0250628 A1 | 9/2015 | Monstadt et al. | |
| 2015/0313737 A1 | 11/2015 | Tippett et al. | |
| 2015/0327843 A1 | 11/2015 | Garrison | |
| 2016/0066921 A1 * | 3/2016 | Seifert | A61L 31/146 606/200 |
| 2016/0135984 A1 | 5/2016 | Rudakov et al. | |
| 2016/0206320 A1 | 7/2016 | Connor | |
| 2016/0206321 A1 | 7/2016 | Connor | |
| 2016/0324668 A1 | 11/2016 | Wallace et al. | |
| 2017/0150971 A1 | 6/2017 | Hines | |
| 2017/0156903 A1 | 6/2017 | Shobayashi | |
| 2017/0189035 A1 | 7/2017 | Porter | |
| 2017/0266023 A1 | 9/2017 | Thomas | |
| 2017/0340333 A1 | 11/2017 | Badruddin et al. | |
| 2017/0367708 A1 | 12/2017 | Mayer et al. | |
| 2018/0049859 A1 | 2/2018 | Stoppenhagen et al. | |
| 2018/0125500 A1 | 5/2018 | Connor | |
| 2018/0125686 A1 | 5/2018 | Lu | |
| 2018/0140305 A1 | 5/2018 | Connor | |
| 2018/0161185 A1 | 6/2018 | Kresslein et al. | |
| 2018/0193025 A1 | 7/2018 | Walzman | |
| 2018/0193026 A1 | 7/2018 | Yang et al. | |
| 2018/0206852 A1 | 7/2018 | Moeller | |
| 2019/0053811 A1 | 2/2019 | Garza et al. | |
| 2020/0060688 A1 | 2/2020 | Andrews et al. | |
| 2020/0060689 A1 | 2/2020 | Andrews et al. | |
| 2021/0100558 A1 | 4/2021 | Andrews et al. | |

FOREIGN PATENT DOCUMENTS

| | | |
|---|---|---|
| JP | 4303419 B2 | 5/2009 |
| JP | 2012101102 A | 5/2012 |
| WO | WO 02/13706 A2 | 2/2002 |
| WO | 2011066962 A1 | 6/2011 |
| WO | 2013078438 A1 | 5/2013 |
| WO | 2016118420 A1 | 7/2016 |
| WO | 2017074411 A1 | 5/2017 |
| WO | 2018051187 A1 | 3/2018 |
| WO | 2018107355 A1 | 6/2018 |

OTHER PUBLICATIONS

Wakhloo, A.K., et al., "Complex-Shaped Platinum Coils for Brain Aneurysms: Higher Packing Density, Improved Biomechanical Stability, and Midterm Angiographic Outcome", University of Massachusetts Medical School, Aug. 2007.

* cited by examiner

ANEURYSM TREATMENT COILS AND ASSOCIATED SYSTEMS AND METHODS OF USE

CROSS-REFERENCE TO RELATED APPLICATION(S)

The present application is a divisional of U.S. patent application Ser. No. 16/108,434, filed Aug. 22, 2018, which is incorporated by reference herein in its entirety.

TECHNICAL FIELD

The present technology relates to implantable devices for treating vascular defects and associated systems and methods of use. In particular, the present technology is directed to occlusive coils for treating cerebral aneurysms.

BACKGROUND

Aneurysms are blood-filled dilations of a blood vessel generally caused by disease or weakening of the blood vessel wall. The wall of the aneurysm may progressively thin, which increases the risk of rupture causing hemorrhagic stroke or even sudden death. There are about 30,000 to 40,000 cases of aneurysmal rupture per year in the United States, accounting for about 5% of all strokes. The prognosis after aneurysmal rupture is poor; the 30-day mortality rate is approximately 45% and a positive functional outcome is achieved in only 40-50% of survivors.

Traditional approaches to preventing aneurysmal rupture often include packing the aneurysm with soft, helically-wound coils to reduce the inflow of blood to the aneurysm and prevent further enlargement and rupture. Conventional coils are created by transforming a metal wire from a primary structure to a secondary structure to a tertiary structure. The primary structure is the "stock" wire, which is fabricated in linear form. The stock wire is wound around a mandrel (also known as the "primary wind" of the coil) to produce the secondary structure of the coil. Finally, the secondary structure can be shaped into any number of configurations (helical, complex, spherical, etc.) and heat set to form the tertiary structure of the coil. When the coil is released into an aneurysm cavity, it assumes its predetermined tertiary structure.

One common tertiary structure used in conventional coils is a helical tertiary structure (i.e., a coil of a coil), which is often referred to simply as a "helical coil". Conventional coils achieve the helical tertiary structure by winding a secondary coil structure around a cylindrical mandrel. Many conventional coils have helical tertiary structures that can only deflect in one direction in response to resistive forces, which has several drawbacks. For example, when a traditional coil meets resistance while being pushed from a microcatheter into the aneurysm cavity, the coil's inability to deflect in multiple directions causes energy to build along the coil. When the coil finally breaks or deflects, the stored energy suddenly releases and often times kicks the microcatheter tip out of position and/or pushes the surrounding, already-implanted coils (and/or portions thereof) out of the aneurysm and into the parent vessel. Such herniated coils may prolong the procedure, and often times require placement of an additional device (such as a stent) and/or require anticoagulant medication. In addition, because traditional helical coils can only bend in one direction, empty space in other directions will not be optimally packed. Thus, the limited ability of traditional helical coils to deflect in multiple directions also leads to incomplete packing of the aneurysm. Clinically, if the aneurysm is not optimally packed, there is a strong likelihood of coil compaction and re-treatment may be needed.

Accordingly, there is a need for improved coils for treating vascular defects.

SUMMARY

The subject technology is illustrated, for example, according to various aspects described below, including with reference to FIGS. 1A-6. Various examples of aspects of the subject technology are described as numbered clauses (1, 2, 3, etc.) for convenience. These are provided as examples and do not limit the subject technology.

Clause 1. An implantable device, comprising:
a coil having a proximal end, a distal end, and a longitudinal axis extending therebetween, the coil formed of an elongated member wound about the longitudinal axis of the coil in a series of contiguous loops,
wherein each of the loops extend around the longitudinal axis between a first end and a second end, the second end disposed at generally the same angular position as the first end about to the longitudinal axis of the coil, and
wherein the elongated member has a longitudinal axis extending along its length, and wherein the elongated member undulates along its longitudinal axis between the first and second ends of at least some of the individual loops.

Clause 2. The implantable device of Clause 1, wherein the elongated member is wound about the longitudinal axis in a first direction, and wherein the elongated member extends distally along the first direction and also proximally along the first direction around the at least some of the individual loops.

Clause 3. The implantable device of Clause 1 or Clause 2, wherein the elongated member is wound about the longitudinal axis in a first direction, and wherein, along the at least some of the individual loops, the elongated member extends along the first direction proximally, then distally, then proximally, and then distally.

Clause 4. The implantable device of any one of Clauses 1 to 3, wherein the first end is at a different axial location than the second end.

Clause 5. The implantable device of any one of Clauses 1 to 4, wherein the elongated member is a coiled wire.

Clause 6. The implantable device of any one of Clauses 1 to 5, wherein the coil has a circular cross-sectional shape.

Clause 7. The implantable device of any one of Clauses 1 to 6, wherein the coil forms a generally tubular structure.

Clause 8. The implantable device of any one of Clauses 1 to 7, wherein the coil has bends along its longitudinal axis in a relaxed state.

Clause 9. The implantable device of any one of Clauses 1 to 8, wherein the coil has a plurality of deflection regions along its longitudinal axis, and wherein the coil is configured to deflect in different directions at different deflection regions.

Clause 10. An implantable device, comprising:
a coil formed of an elongated member wound about a longitudinal axis of the coil in a series of contiguous loops, each of the loops beginning and ending at generally the same angular position about the longitudinal axis of the coil, wherein, along at least some of the individual loops, the elongated member has a plurality of alternating peaks and valleys, the valleys being axially spaced apart from the peaks.

Clause 11. The implantable device of Clause 10, wherein the elongated member is a coiled wire.

Clause 12. The implantable device of Clause 10 or Clause 11, wherein the coil has a circular cross-sectional shape.

Clause 13. The implantable device of any one of Clauses 10 to 12, wherein the coil forms a generally tubular structure.

Clause 14. The implantable device of any one of Clauses 10 to 13, wherein the coil is generally cylindrical.

Clause 15. The implantable device of any one of Clauses 10 to 14, wherein the coil has bends along its longitudinal axis in a relaxed state.

Clause 16. The implantable device of any one of Clauses 10 to 15, wherein the coil has a plurality of deflection regions along its longitudinal axis, and wherein the coil is configured to deflect in different directions at different deflection regions.

Clause 17. A method for forming an implantable device, the method comprising:
  winding an elongated member about a shaft portion of a mandrel, the shaft portion disposed along the mandrel between a proximal forming member and a distal forming member;
  axially constraining the wound member on the shaft between the proximal and distal forming members such that a first circumferential section of the wound member is urged distally and a second circumferential section of the wound member is urged proximally; and
  heat-setting the elongated member while axially constrained on the mandrel.

Clause 18. The method of Clause 17, wherein the shaft portion of the mandrel is linear and has a generally constant diameter.

Clause 19. The method of Clause 17 or Clause 18, wherein the shaft portion of the mandrel has a generally constant diameter along its length.

Clause 20. The method of any one of Clauses 17 to 19, wherein the wound member is axially constrained on the shaft between an undulating, proximal face of the distal forming member and an undulating, distal face of the proximal forming member.

Clause 21. An implantable device, comprising:
  a distal end, a proximal end, and a longitudinal axis extending therebetween; and
  an elongated member wound about the longitudinal axis to form a series of loops, wherein along at least some of the loops, the elongated member includes a first peak and a second peak axially offset from the first peak, the first peak being axially between the second peak and the proximal end, and wherein the first peak is convex towards the distal end, and the second peak is convex towards the proximal end.

Clause 22. The implantable device of Clause 21, wherein, for a given one of the loops, the first peak and the second peak are free to move relative to one another.

Clause 23. The implantable device of Clause 21 or Clause 22, wherein, for a given one of the loops, the first peak is about 360 degrees from the second peak about the longitudinal axis of the device.

Clause 24. The implantable device of any one of Clauses 21 to 23, wherein the elongated member is a coiled wire.

Clause 25. The implantable device of any one of Clauses 21 to 25, wherein the device has a circular cross-sectional shape in a relaxed state.

Clause 26. The implantable device of any one of Clauses 21 to 26, wherein, for a given one of the loops, the first peak is not intertwined with the second peak.

Clause 27. The implantable device of any one of Clauses 21 to 26, wherein the device forms a generally tubular structure.

Clause 28. The implantable device of any one of Clauses 21 to 27, wherein the device has a predetermined shape in a relaxed, unconstrained state.

Clause 29. The implantable device of any one of Clauses 21 to 28, wherein the device has a plurality of deflection regions along its longitudinal axis, and wherein the device is configured to deflect in different directions at different deflection regions.

Clause 30. An implantable device, comprising:
  a distal end, a proximal end, and a longitudinal axis extending therebetween; and
  an elongated member wound about the longitudinal axis to form a series of loops, the elongated member having a longitudinal axis extending along its length, and wherein the elongated member undulates along its longitudinal axis along each loop,
  wherein each of the loops has a first end and a second, and wherein, for at least some of the loops, the first end extends towards the second end, and vice versa.

Clause 31. The implantable device of Clause 30, wherein immediately adjacent loops are spaced apart from one another.

Clause 32. The implantable device of Clause 30 or Clause 31, wherein the implantable device is configured to be positioned within a cerebral aneurysm.

Clause 33. The implantable device of any one of Clauses 30 to 32, wherein the elongated member is a coiled wire.

Clause 34. The implantable device of any one of Clauses 30 to 33, wherein the elongated member forms a generally tubular structure.

Clause 35. The implantable device of any one of Clauses 30 to 34, wherein the device has a circular cross-sectional shape in a relaxed state.

Clause 36. The implantable device of any one of Clauses 30 to 35, wherein the device has a predetermined shape in a relaxed, unconstrained state.

Clause 37. The implantable device of any one of Clauses 30 to 36, wherein the device has a plurality of deflection regions along its longitudinal axis, and wherein the device is configured to deflect in different directions at different deflection regions.

Clause 38. A method for forming an implantable device, the method comprising:
  winding an elongated member about a mandrel to form a series of loops, wherein along at least some of the loops, the elongated member includes a first peak and a second peak axially offset from the first peak, the first peak being axially between the second peak and the proximal end, and wherein the first peak is convex towards the distal end, and the second peak is convex towards the proximal end; and
  heat-setting the elongated member while wound around the mandrel.

Clause 39. The method of Clause 38, wherein the elongated member is a coil.

Clause 40. The method of Clause 38 or Clause 39, wherein the mandrel has a substantially constant cross-sectional dimension along its length.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology relates to occlusive coils and associated systems and methods of use. Some embodiments of the present technology, for example, are directed to occlusive coils for treating cerebral aneurysms. Specific details of several embodiments of the technology are described below with reference to FIGS. 1A-6.

Figures 1A, 1B, 1C:
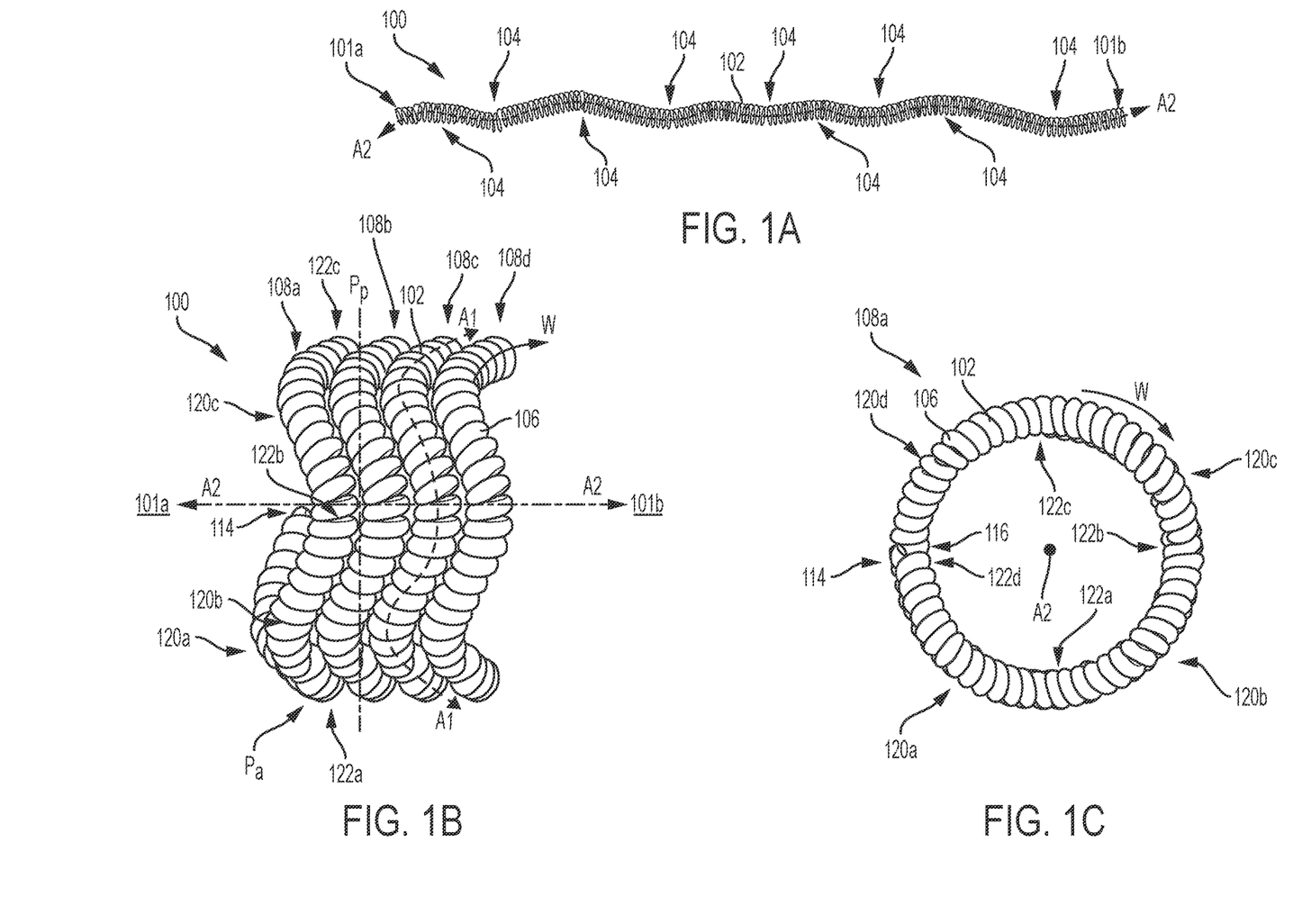
FIG. 1A depicts an occlusive coil in accordance with the present technology, shown in a relaxed state.
FIG. 1B is an enlarged side view of a portion of the coil shown in FIG. 1A.
FIG. 1C is an enlarged end view of the coil shown in FIG. 1A.

FIG. 1A shows an occlusive coil 100 (or "coil 100") configured in accordance with the present technology, shown in a relaxed state (i.e., the theoretical three-dimensional configuration assumed by the coil 100 as it would exist with no outside forces on it in its tertiary configuration). The coil 100 has a proximal end 101a, a distal end 101b, and a longitudinal axis A2 extending therebetween. As shown in FIG. 1A, the coil 100 is formed of an elongated member 102 wound about the longitudinal axis A2 and heat set in a novel helical tertiary structure. Unlike conventional helical coils that are generally straight in a relaxed state, the coil 100 has bends along its longitudinal axis A2 between a plurality of deflection regions 104. As used herein with respect to the coils of the present technology, a "deflection region" is an area that is more predisposed to bending than the portion of the coil that is not part of a deflection region. One or more deflection regions may be predisposed to bending in one or more first directions and one or more different deflection regions may be predisposed to bending in one or more second directions. The one or more first directions may be the same or different from the one or more second directions. The deflection regions 104 allow the coil 100 to bend in multiple directions, which provides several advantages over conventional helical coils that are limited to a single bend direction. For example, the coil's 100 ability to bend in multiple directions allows the coil 100 to bend sooner in response to resistive forces during deployment. As such, the coil 100 builds up less energy during deployment than a conventional coil (if any at all), thus eliminating or greatly reducing the severity of the effects of a sudden "break" or deflection. As a result, the coil 100 of the present technology reduces the potential for catheter kick-out and coil herniation, thus reducing procedure complications. Moreover, the coil's ability to deflect in multiple directions allows it to seek and pack empty space within a coil-packed aneurysm, thereby increasing the aneurysm packing volume and reducing the chance of retreatment due to coil compaction.

FIG. 1B is an enlarged side view of a portion of the coil 100, and FIG. 1C is an end view of the coil 100. Referring to FIGS. 1A-1C together, the elongated member 102 may be wound about the longitudinal axis A2 of the coil 100 in a series of contiguous loops or windings, four of which are shown in FIG. 1B and labeled 108a-d. Each of the loops extend around the longitudinal axis A2 between a first end and a second end (labeled 114, 116 for loop 108a; second end 116 not visible in FIG. 1B), where the second end is disposed approximately 360 degrees from the first end about the longitudinal axis A2 of the coil 100. That is, the first and second ends are disposed at generally a same angular position relative to the longitudinal axis A2 of coil 100. As shown in FIG. 1C, in some embodiments the coil 100 has a circular cross-sectional shape. In other embodiments, the coil 100 may have other suitable cross-sectional shapes (e.g., oval, square, triangular, polygonal, etc.). The cross-sectional shape of the coil 100 may be generally the same or vary along the length of the coil 100 and/or from loop to loop. Likewise, the diameter of the coil 100 may be generally constant or vary along the length of the coil 100 and/or from loop to loop (usually between about 2 mm and about 20 mm). In some embodiments, the coil 100 has a generally cylindrical shape.

Figure 2A:
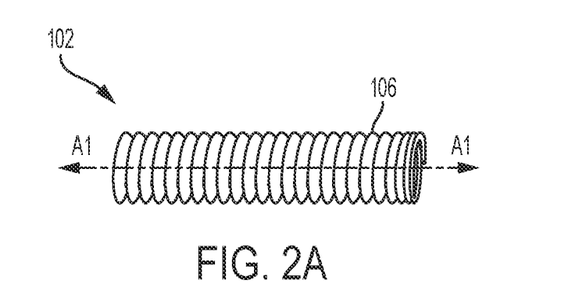
FIGS. 2A-2C are different elongated members used for forming the occlusive coils of the present technology.
Figure 2B:
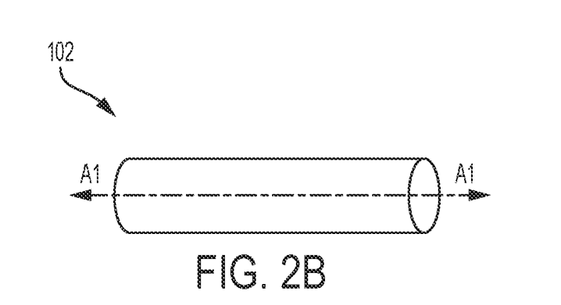
Figure 2C:
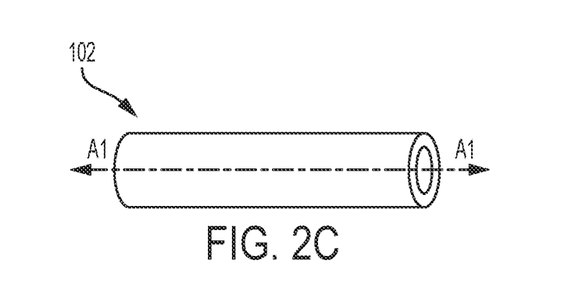

In some embodiments, such as that shown in FIGS. 1A-1C, the elongated member 102 is also a coiled structure. For example, FIG. 2A shows the elongated member 102 in its secondary form, prior to being wound and heat set to form the helical tertiary structure of FIGS. 1A-1C. In such embodiments where the elongated member 102 is a coil, the elongated member 102 may be formed of a wire 106 wound about a longitudinal axis A1 to form a generally tubular structure, as shown in FIG. 2A. The elongated member 102 may have a pitch that is constant or varies over its length. Likewise, the coil 100 may have a pitch that is constant or varies over its length. In some embodiments, the elongated member 102 does not comprise a coil and instead comprises an uncoiled, solid wire (FIG. 2B) or an uncoiled tube (FIG. 2C). The elongated member 102 may be made of any material suitable for forming an occlusive device, such as nitinol, platinum, rhodium, palladium, tungsten, gold, silver, cobalt-chromium, and/or various alloys of these materials.

As best shown in FIGS. 1B and 1C, the elongated member 102 may undulate along its longitudinal axis A1 as it winds around the longitudinal axis A2 of the coil 100, forming a plurality of alternating peaks (closer to the distal end 101a of the coil 100) and valleys (closer to the proximal end 101a of the coil 100). The valleys are at a different location along the longitudinal axis A1 than the peaks (i.e., are axially spaced apart from the peaks). For example, for loop 108a, in the direction of the wind W (clockwise or counterclockwise), the elongated member 102 extends proximally from the first end 114 to a first valley 120a, then distally to a first peak 122a, then proximally to a second valley 120b, then distally to a second peak 122b, then proximally to a third valley 120c, then distally to a third peak 122c, then proximally to a fourth valley 120d (not visible in FIG. 1B), then distally to a fourth peak 122d (not visible in FIG. 1B), which coincides with the second end 116 of loop 108a. Stated otherwise, when traveling in a direction of the wind W around a given loop, the loop does not consistently progress distally or proximally, but rather undulates so that along certain portions of its length, the loop becomes progressively more proximal, and along other portions of its length the loop becomes progressively more distal. Although the first and second ends 114, 116 may be generally aligned circumferentially, the first and second ends 114, 116 are disposed at different axial locations.

Although FIGS. 1B and 1C show a coil embodiment having four peaks and four valleys per loop, in some embodiments the coil 100 has more or fewer peaks and/or more or fewer valleys in a given loop. For example, in some embodiments the coil has one, two, three, four, five, six, seven, eight, etc. peaks per loop and one, two, three, four, five, six, seven, eight, etc. valleys per loop. The loops may have the same or a different number of peaks, and the loops may have the same or a different number of valleys. In addition, the amplitude of the peaks may be the same or different along a given loop and/or amongst the loops, and the amplitude of the valleys may be the same or different along a given loop and/or amongst the loops. Moreover, the peaks and valleys can have the same or different amplitudes.

In some embodiments, all of the loops have an undulating shape, and in some embodiments at least some of the loops have a non-undulating shape (i.e., a straight helical turn). Moreover, in some embodiments successive loops are nested, i.e., immediately adjacent to and/or in contact with one another along most of their circumferential lengths (as shown in FIG. 1B). In other embodiments one or more successive loops are spaced apart along all or a portion of their respective circumferential lengths. In particular embodiments, the coil 100 includes both nested and spaced apart loops. In addition, the number of loops may vary depending on the desired length of the coil 100. The length of the coil 100, for example, may be from about 2 cm to about 80 cm, depending on the application for which it will be used.

Figure 3:
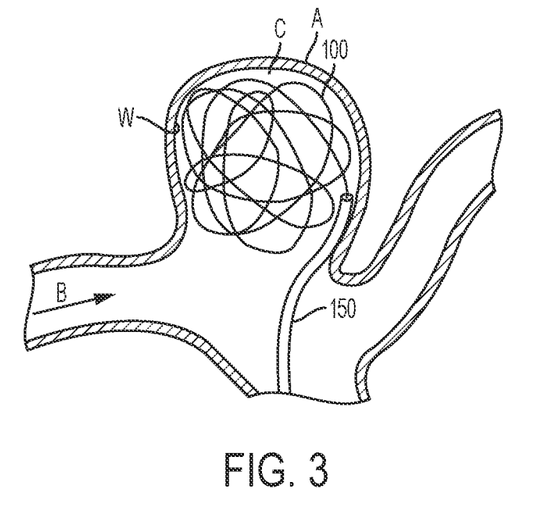
FIG. 3 shows an occlusive coil of the present technology being deployed within an aneurysm.

FIG. 3 shows the coil 100 in a deployed state positioned within an aneurysm A. As used herein, "deployed configuration" or "deployed state" refers to the shape of the coil 100 after it has been deployed from a delivery catheter (e.g., a microcatheter). The deployed configuration of a particular device may differ, depending on whether the device is deployed into the open, or whether it is deployed into a body cavity which may influence its three-dimensional structure. As shown in FIG. 3, the coil 100 may be intravascularly delivered to the aneurysm cavity C (such as a cerebral aneurysm) via a delivery catheter (e.g., a microcatheter). With the distal tip of the catheter 150 positioned within the aneurysm A (or at least at the neck of the aneurysm A), the coil 100 is pushed distally from the catheter tip into the cavity C. As additional coils (or additional length of a given coil) are delivered into the cavity C and the packed volume increases, subsequent coils 100 will experience increased resistance when exiting the catheter. Unlike traditional helical coils that cannot bend in multiple directions in response to this resistance, the coil 100 can bend/deflect in multiple directions. Thus, as previously mentioned, the coil 100 of the present technology reduces the potential for catheter kick-out and coil herniation, thus reducing procedure complications. Moreover, the ability to deflect in multiple directions allows the coil 100 to seek and pack empty space within a coil-packed aneurysm, thereby increasing the aneurysm packing volume and reducing the chance of retreatment due to coil compaction.

Figure 4A:
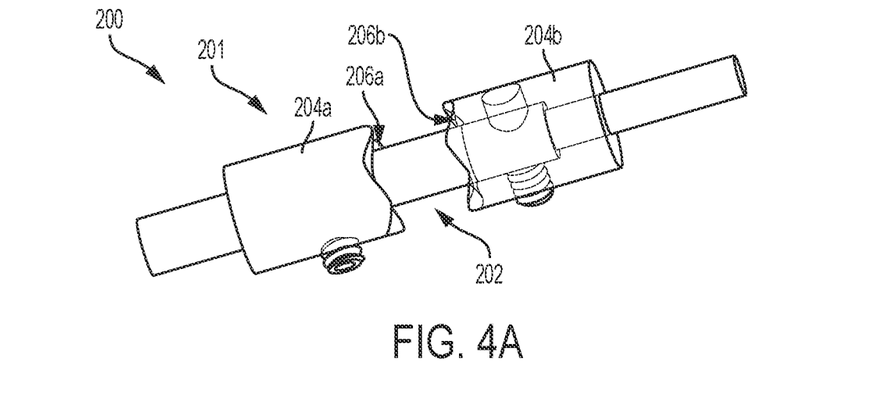
FIGS. 4A and 4B illustrate a method for manufacturing an occlusive coil in accordance with some embodiments of the present technology.
Figure 4B:
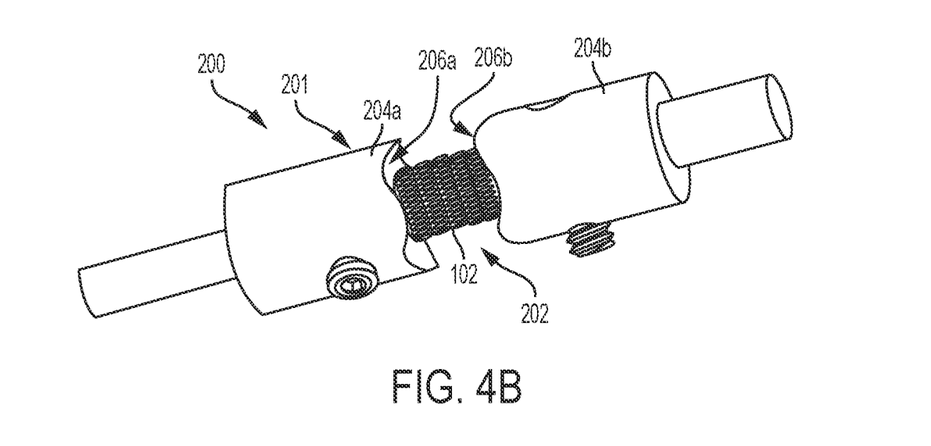

FIGS. 4A and 4B illustrate a system 200 and method for manufacturing occlusive coils in accordance with some embodiments of the present technology, including coil 100. As shown in FIGS. 4A and 4B, the system 200 may include a mandrel 201 having a shaft portion 202 and a proximal forming member 204a and a distal forming member 204b on either side of the shaft portion 202. In some embodiments, including the embodiment shown in FIGS. 4A and 4B, the shaft portion 202 is generally cylindrical (i.e., has a generally circular cross-section and a constant diameter along its length). In other embodiments, the shaft portion 202 can have other cross-sectional shapes and/or have a varying cross-sectional dimension along its length.

The proximal forming member 204a may have an undulating, distal face 206a and the distal forming member 204b may have an undulating, proximal face 206b that faces the distal face 206a of the proximal forming member 204a. As shown in FIGS. 4A and 4B, the distal and proximal faces 206a, 206b may have a complementary topography such that the peaks of the proximal face 206b are circumferentially aligned with the valleys of the distal face 206, and vice versa. The undulations of the distal and proximal faces, 206a, 206b may be curved (as in FIGS. 4A and 4B), or all or a portion of the undulations may be linear.

In some embodiments of making the coil 100, the elongated member 102 may be wound around the shaft portion 202 of the mandrel 201 with a proximal end of the wound member spaced apart from the proximal face 206b and the distal end of the wound member spaced apart from the distal face 206a. The proximal and distal forming members 204a, 204b may then be moved towards one another to contact and exert axially compressive forces on the proximal and distal ends of the wound member, thereby forcing the wound member to take the undulating shape of the faces 206a, 206b along its entire length. For example, the proximal and distal forming members 204a, 204b may urge a first circumferential section of the wound member distally (thereby forming the peaks) and a second circumferential section of the wound member proximally (thereby forming the valleys). While in this axially constrained configuration, the elongated member 102 is then heat-set to form the coil 100.

Figure 5A:
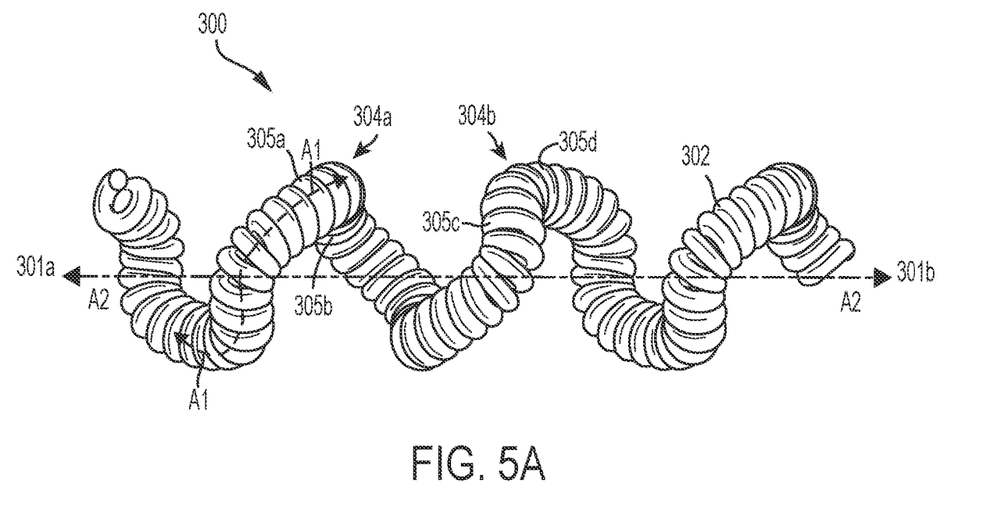
FIG. 5A depicts an occlusive coil in accordance with the present technology, shown in a relaxed state.
Figure 5B:
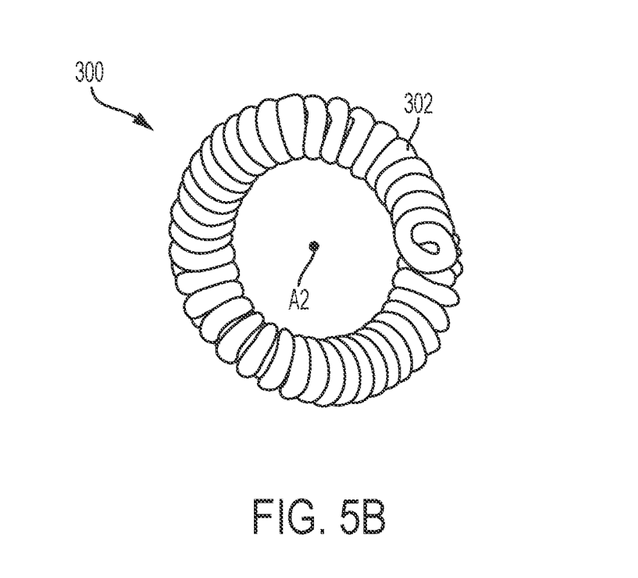
FIG. 5B is an enlarged end view of the coil shown in FIG. 5A.

FIG. 5A shows a portion of the length of an occlusive coil 300 (or "coil 300") configured in accordance with the present technology, shown in a relaxed, unconstrained state, and FIG. 5B is an end view of the coil 300. Referring to FIGS. 5A and 5B together, the coil 300 has a proximal end 301a, a distal end 301b, and a longitudinal axis A2 extending therebetween. As shown in FIG. 5A, the coil 300 is formed of an elongated member 302 wound about the longitudinal axis A2 and heat set in a novel helical tertiary structure. Similar to coil 100, the coil 300 is configured to bend in multiple directions, which provides several advantages over conventional, unidirectional-bending helical coils, such as a reduced potential for catheter kick-out and coil herniation, and increased aneurysm packing volume potential.

In some embodiments, including that shown in FIGS. 5A and 5B, the elongated member 302 is also a coiled structure. For example, similar to the elongated member 102 shown in FIG. 2A, the elongated member 302 may have a secondary form prior to being wound and heat set to form the helical tertiary structure of FIGS. 5A and 5B. In such embodiments where the elongated member 302 is a coil, the elongated member 302 may be formed of a wire (such as wire 106) wound about a longitudinal axis A1 to form a generally tubular structure, as shown in FIG. 2A. The elongated member 302 may have a pitch that is constant or varies over its length. Likewise, the coil 300 may have a pitch that is constant or varies over its length. In some embodiments, the elongated member 302 does not comprise a coil and instead comprises an uncoiled, solid wire (FIG. 2B) or an uncoiled tube (FIG. 2C). The elongated member 302 may be made of any material suitable for forming an occlusive device, such as nitinol, platinum, rhodium, palladium, tungsten, gold, silver, cobalt-chromium, and/or various alloys of these materials.

As best shown in FIG. 5B, the coil 300 may have a circular cross-sectional shape. In some embodiments, the coil 300 may have other suitable cross-sectional shapes (e.g., oval, square, triangular, polygonal, etc.). The cross-sectional shape of the coil 300 may be generally the same or vary along the length of the coil 300 and/or from loop to loop. Likewise, the diameter of the coil 300 may be generally constant or vary along the length of the coil 300 and/or from loop to loop (usually between about 2 mm and about 20 mm).

The elongated member 302 may be wound about the longitudinal axis A2 of the coil 300 in a series of contiguous loops or windings. Each of the loops extend around the longitudinal axis A2 between a first end and a second end that is disposed about 360 degrees from the first end about the longitudinal axis A2 of the coil 300. The elongated member 302 may undulate along its longitudinal axis A1 as it winds around the longitudinal axis A2 of the coil 100, forming a plurality of alternating peaks. Along a given loop, the elongated member 302 may start at a first peak 304a and end at a second peak 304b that is axially offset from the first peak 304a.

As shown in FIG. 5A, the first peak 304a may form a curved structure or length of the elongated member 302 that is convex towards the distal end 301b of the coil 300. In those embodiments where the elongated member 302 is a coil (such as the embodiment shown in FIG. 5A), the curved structure of the first peak 304a may comprise multiple turns of the wire that forms the coil (such as wire 106 in FIG. 2A). For example, the curved structure may extend between end turn 305a and end turn 305b and include the one or more intermediate turns between end turns 305a and 305b. In some embodiments, at least one point on the wire along the one or more intermediate turns is more distal than any point on either of end turns 305a or 305b. In some embodiments, the entire length of the wire along one or more intermediate turns is more distal than any point on either of end turns 305a or 305b.

The second peak 304b may form a curved structure or length that is convex towards the proximal end 301a of the coil 300. The curved structure of the second peak 304b may comprise multiple turns of the wire that forms the coil (such as wire 106 in FIG. 2A). For example, the curved structure may extend between end turn 305c and end turn 305d and include the one or more intermediate turns between end turns 305c and 305d. In some embodiments, at least one point on the wire along the one or more intermediate turns is more proximal than any point on either of end turns 305c or 305d. In some embodiments, the entire length of the wire along one or more intermediate turns is more proximal than any point on either of end turns 305c or 305d.

Referring still to FIG. 5A, the first and second peaks 304a, 304b may extend towards one another. The axial distance between the second peak 304b and the distal end 301b of the coil 300 may be less than the distance between the first peak 304a and the distal end 301b. Likewise, the distance between the first peak 304a and the proximal end 301a may be less than the distance between the second peak 304b and the proximal end 301a. As shown in FIG. 5A, the adjacent loops of the coil 300 may be spaced apart from one another along the longitudinal axis A2 of the coil.

The coil 300 may have any number of loops (e.g., two, three, four, five, six, etc.). The coil 300 may have one, two, three, four, five, six, seven, eight, etc. peaks per loop. The loops may have the same or a different number of peaks, and the loops may have the same or a different number of valleys. In addition, the amplitude of the peaks may be the same or different along a given loop and/or amongst the loops. Moreover, the peaks can have the same or different amplitudes. In some embodiments, all of the loops have an undulating shape, and in some embodiments at least some of the loops have a non-undulating shape (i.e., a straight helical turn).

In use, the coil 300 may be delivered to an aneurysm (such as a cerebral aneurysm) as described above for coil 100 with reference to FIG. 3.

Figure 6:
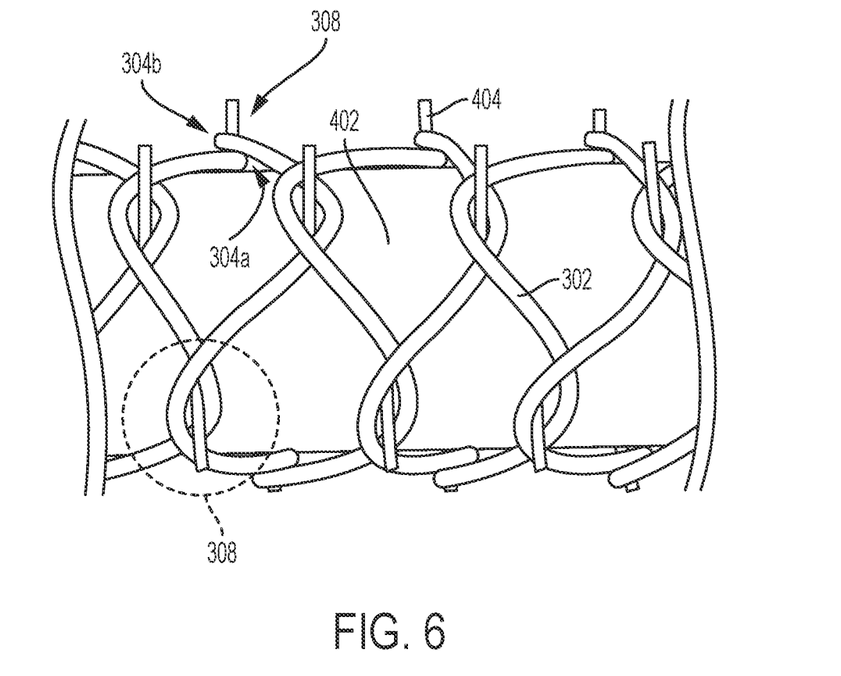
FIG. 6 shows a portion of the occlusive coil positioned on a mandrel during manufacturing of the coil.

FIG. 6 shows a portion of the elongated member 302 positioned on a mandrel 402 during manufacturing of the coil 300. (For ease of viewing the tertiary structure of the coil 300, the elongated member 302 is shown as a non-coiled wire in FIG. 6.) As shown in FIG. 6, the mandrel 402 may have a series of circumferentially- and axially-spaced posts 404 (only one labeled in FIG. 6 for ease of illustration), and the elongated member 302 may be wound about the mandrel 402 and around the posts 404. In some embodiments, including the embodiment shown in FIG. 6, the shaft 402 is generally cylindrical (i.e., has a generally circular cross-section and a constant diameter along its length). In other embodiments, the shaft 402 can have other cross-sectional shapes and/or have a varying cross-sectional dimension along its length. While in this wound configuration, the elongated member 302 is then heat-set to form the coil 300.

While on the mandrel, the coil 300 may include a plurality of overlap regions 308 spaced apart about its circumference (only one overlap region is labeled in FIG. 6). Within the overlap regions 308, the first peak 304a may be axially aligned with or extend beyond the second peak 306b. The first and second peaks 304a, 304b are not intertwined such that the first peak 304a is free to move relative to the second peak 306b, and vice versa. As such, after being heat set and removed from the mandrel, the coil 300 assumes a relaxed state (as shown in FIG. 5A) in which at least some of the adjacent loops of the coil 300 separate from one another, and the previously-overlapping first and second peaks 304a, 304b are spaced apart. As such, the portions of the first and second peaks 304a, 304b that extended beyond one another when on the mandrel now form the convex structures that point towards one another as described in FIG. 5A. In some embodiments, no portion of the elongated member 302 is intertwined with no other portion of the elongated member 302. In some embodiments, some portions of the elongated member 302 are intertwined.

Conclusion

Although many of the embodiments are described above with respect to systems, devices, and methods for treating cerebral aneurysms, the technology is applicable to other applications and/or other approaches, such as the treatment of other aneurysms or vascular defects. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-6.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for forming an implantable device, the method comprising:
    winding an elongated member about a shaft portion of a mandrel, the shaft portion disposed along the mandrel between a proximal forming member and a distal forming member;
    axially constraining the wound member on the shaft between the proximal and distal forming members such that a first circumferential section of the wound member is urged distally and a second circumferential section of the wound member is urged proximally; and
    heat-setting the elongated member while positioned on the mandrel.

2. The method of claim 1, wherein the shaft portion of the mandrel is linear and has a generally constant diameter.

3. The method of claim 1, wherein the shaft portion of the mandrel has a generally constant diameter along its length.

4. The method of claim 1, wherein the wound member is axially constrained on the shaft between an undulating, proximal face of the distal forming member and an undulating, distal face of the proximal forming member.

5. The method of claim 4, wherein the undulating, proximal face of the distal forming member and the undulating, distal face of the proximal forming member have complementary topographies.

6. The method of claim 4, wherein the undulations of the distal and proximal faces are curved.

7. The method of claim 1, wherein the elongated member is a coiled wire.

8. A method for forming an implantable device, the method comprising:
    obtaining a forming assembly comprising first and second forming members disposed on a shaft, wherein the first and second forming members are spaced apart along the shaft;
    winding an elongated member about the shaft between the first and second forming members in a series of loops;
    compressing the wound member between the first and second forming members such that, along at least some of the individual loops, the elongated member has a plurality of alternating peaks and valleys, the valleys being axially spaced apart from the peaks; and
    setting a shape of the elongated member while positioned on the forming assembly.

9. The method of claim 8, wherein the wound member is compressed between a distal face of the first forming member and a proximal face of the second forming member.

10. The method of claim 9, wherein each of a distal face of the first forming member and a proximal face of the second forming member comprises peaks and valleys.

11. The method of claim 10, wherein the peaks of the distal face of the first forming member are circumferentially aligned with the valleys of the proximal face of the second forming member.

12. The method of claim 10, wherein the valleys of the distal face of the first forming member are circumferentially aligned with the peaks of the proximal face of the second forming member.

13. The method of claim 10, wherein the distal face of the first forming member comprises the same number of peaks and valleys as the proximal face of the second forming member.

14. The method of claim 10, wherein an amplitude of the peaks is the same as an amplitude of the valleys.

15. The method of claim 8, wherein the elongated member comprises a coiled wire.

16. The method of claim 8, wherein compressing the elongated member comprises moving the first and second forming members toward each other and into contact with the elongated member.

17. The method of claim 8, wherein setting a shape of the elongated member comprises applying heat to the elongated member.

18. A method for forming an implantable device, the method comprising:
    winding an elongated member about a central portion of mandrel in a series of loops, the central portion disposed between a proximal forming member and a distal forming member;
    conforming the wound member to an oscillating, proximal face of the distal forming member and an oscillating, distal face of the proximal forming member such that the wound member oscillates axially along at least some of the loops; and
    heat-setting the elongated member while positioned on the mandrel.

19. The method of claim 18, wherein conforming the wound member comprises moving the proximal and distal forming members into contact with the elongated member.

20. The method of claim 19, wherein the central portion is generally cylindrical.

* * * * *